(12) United States Patent
Calvin

(10) Patent No.: US 10,585,028 B2
(45) Date of Patent: Mar. 10, 2020

(54) METHOD AND APPARATUS FOR OPTICAL ANALYSIS

(71) Applicant: Charted Scientific, Inc., Santa Cruz, CA (US)

(72) Inventor: Edward Calvin, Austin, TX (US)

(73) Assignee: Charted Scientific, Inc., Austin, TX (US)

( * ) Notice: Subject to any disclaimer, the term of this patent is extended or adjusted under 35 U.S.C. 154(b) by 0 days.

(21) Appl. No.: 16/049,727

(22) Filed: Jul. 30, 2018

(65) Prior Publication Data
US 2019/0120746 A1 Apr. 25, 2019

Related U.S. Application Data

(60) Provisional application No. 62/575,207, filed on Oct. 20, 2017.

(51) Int. Cl.
*G01N 15/14* (2006.01)
*G01N 15/10* (2006.01)

(52) U.S. Cl.
CPC ....... *G01N 15/1404* (2013.01); *G01N 15/147* (2013.01); *G01N 15/1434* (2013.01); *G01N 15/1436* (2013.01); *G01N 2015/1006* (2013.01); *G01N 2015/1409* (2013.01)

(58) Field of Classification Search
CPC ........... G01N 15/1404; G01N 15/1436; G01N 15/1438
See application file for complete search history.

(56) References Cited

U.S. PATENT DOCUMENTS

| | | |
|---|---|---|
| 4,683,212 A | 7/1987 | Uffenheimer |
| 5,192,980 A | 3/1993 | Dixon et al. |
| 5,248,876 A | 9/1993 | Kerstens et al. |
| 5,381,224 A | 1/1995 | Dixon et al. |
| 5,418,371 A | 5/1995 | Aslund |
| 5,731,874 A | 3/1998 | Maluf |

(Continued)

FOREIGN PATENT DOCUMENTS

KR 101513604 B1 4/2015

OTHER PUBLICATIONS

PCT Notification of Transmittal of International Search Report and the Written Opinion of the International Searching Authority dated Mar. 6, 2019, issued from the International Searching Authority in related PCT Application No. PCT/US2018/056482, (17 pages).

(Continued)

*Primary Examiner* — Hugh Maupin
(74) *Attorney, Agent, or Firm* — David McEwing

(57) ABSTRACT

An optical analysis apparatus, including: a sample delivery system from which a liquid sample may be delivered in operation; a flow cell defining a channel through which, in operation, the delivered liquid sample may flow at a controllable rate, the channel including an optical analysis region; an illumination source focused on a portion of the optical analysis region that, in operation, illuminates a single particle at a time in a stream of the sample wider than the single particle; a detector that, in operation, detects light resulting from the illumination of the sample and outputting a signal representative of the detected light; and an analysis system receiving the representative signal.

21 Claims, 10 Drawing Sheets

(56) References Cited

U.S. PATENT DOCUMENTS

| | | | |
|---|---|---|---|
| 5,847,400 | A | 12/1998 | Kain et al. |
| 6,097,025 | A | 8/2000 | Modlin et al. |
| 6,097,485 | A | 8/2000 | Lievan |
| 6,177,277 | B1 | 1/2001 | Soini |
| 6,684,092 | B2 | 1/2004 | Zavislan |
| 6,804,000 | B2 | 10/2004 | Roorda et al. |
| 6,858,852 | B2 | 2/2005 | Wolleschensky et al. |
| 6,875,578 | B2 | 4/2005 | Giulano et al. |
| 6,891,613 | B2 | 5/2005 | Wolleschensky |
| 6,927,888 | B2 | 8/2005 | Garcia et al. |
| 6,947,133 | B2 | 9/2005 | Wolleschensky |
| 8,454,512 | B2 | 6/2013 | Wang et al. |
| 8,639,012 | B2 | 1/2014 | Heng et al. |
| 9,063,334 | B2 | 6/2015 | Schultz |
| 9,068,978 | B2 | 6/2015 | Brucki et al. |
| 9,091,654 | B2 | 7/2015 | Heng et al. |
| 9,360,410 | B2 | 6/2016 | King et al. |
| 9,470,700 | B2 | 10/2016 | Uchikawa |
| 9,500,644 | B2 | 11/2016 | Schilffarth et al. |
| 9,964,539 | B2 | 5/2018 | Hamasaki et al. |
| 2002/0131047 | A1 | 9/2002 | Zarrabian et al. |
| 2005/0275839 | A1* | 12/2005 | Robinson ............ G01J 3/2803 356/318 |
| 2005/0280817 | A1* | 12/2005 | Horchner ............ G01J 3/2803 356/318 |
| 2006/0077383 | A1 | 4/2006 | Knebel et al. |
| 2007/0035818 | A1 | 2/2007 | Bahatt et al. |
| 2009/0170214 | A1 | 7/2009 | Meek et al. |
| 2010/0032584 | A1* | 2/2010 | Dayong ............ G01N 15/14 250/459.1 |
| 2010/0177308 | A1 | 7/2010 | Bohle et al. |
| 2012/0154801 | A1 | 6/2012 | Carron et al. |
| 2012/0183441 | A1 | 7/2012 | Schilffarth et al. |
| 2012/0307244 | A1 | 12/2012 | Sharpe et al. |
| 2014/0038259 | A1 | 2/2014 | Chen |
| 2014/0065637 | A1 | 3/2014 | Kirk et al. |
| 2014/0152986 | A1 | 6/2014 | Trainer |
| 2014/0329265 | A1 | 11/2014 | Wanders et al. |
| 2014/0339446 | A1* | 11/2014 | Yamamoto ......... G01N 15/1434 250/576 |
| 2015/0024476 | A1* | 1/2015 | Butler ............ B01L 3/502761 435/288.7 |
| 2015/0355024 | A1 | 12/2015 | Goldring et al. |
| 2017/0322133 | A1 | 11/2017 | Trainer |
| 2018/0038783 | A1* | 2/2018 | Yamamoto ......... G01N 15/1459 |
| 2018/0195124 | A1 | 7/2018 | Gonzalez et al. |
| 2018/0266884 | A1 | 9/2018 | Xu |
| 2018/0372634 | A1 | 12/2018 | Krishnamoorthy et al. |
| 2019/0025210 | A1 | 1/2019 | Neijzen et al. |
| 2019/0089914 | A1 | 3/2019 | Richarte et al. |
| 2019/0120753 | A1 | 4/2019 | Prater et al. |
| 2019/0120807 | A1 | 4/2019 | Warner et al. |
| 2019/0129094 | A1 | 5/2019 | Lin |

OTHER PUBLICATIONS

Haasen, Dorothea, et al. "Comparison of G-protein coupled receptor desensitization-related B-arrestin redistribution using confocal and non-confocal imaging." Combinatorial chemistry & high throughput screening 9.1 (2006): 37-47. https://booksc.xyz/book/43685891/18f78f.

Zucker, Robert M. "Quality assessment of confocal microscopy slide based systems: performance." Cytometry Part A: the journal of the International Society for Analytical Cytology 69.7 (2006): 659-676. https://onlinelibrary.wiley.com/doi/pdf/10.1002/cyto.a.20314.

He, Wei, et al. "In vivo quantitation of rare circulating tumor cells by multiphoton intravital flow cytometry." Proceedings of the National Academy of Sciences 104.28 (2007): 11760-11765. https://www.pnas.org/content/pnas/104/28/11760.full.pdf.

Fan, G. Y., et al. "Video-rate scanning two-photon excitation fluorescence microscopy and ratio imaging with cameleons." Biophysical journal 76.5 (1999): 2412-2420. http://citeseerx.ist.psu.edu/viewdoc/download?.

McConnell, Gail, and Erling Riis. "Two-photon laser scanning fluorescence microscopy using photonic crystal fiber." Journal of biomedical optics 9.5 (2004):922-928.5 https://www.spiedigitallibrary.org/journalArticle/Download?fullDOI=10.1117/1.1778734.

Denk, Winfried, James H. Strikler, and Watt W. Webb. "Two-photon laser scanning fluorescence microscopy." Science 2248.4951 (1990): 73-76. https://pdfs.semanticscholar.org/566e/2663f897523-d3309138a846e687626430771.pdf.

\* cited by examiner

METHOD AND APPARATUS FOR OPTICAL ANALYSIS

CROSS-REFERENCE TO RELATED APPLICATIONS

Priority to U.S. Provisional Application 62/575,207, filed Oct. 20, 2017, entitled, "Novel Method for Optical Analysis of Particle Suspended in a Liquid Medium Using Fluorescent and Scattered Light", and naming Edward Calvin as inventor, is hereby claimed under 35 U.S.C. § 119 (e). This application is hereby incorporated by reference for all purposes as if expressly set forth herein.

Priority to U.S. Provisional Application 62/636,024, filed Feb. 27, 2018, entitled, "Novel Method for Optical Analysis of Particle Suspended in a Liquid Medium Using Fluorescent and Scattered Light", and naming Edward Calvin as inventor, is hereby claimed under 35 U.S.C. § 119 (e). This application is hereby incorporated by reference for all purposes as if expressly set forth herein.

STATEMENT REGARDING FEDERALLY SPONSORED RESEARCH OR DEVELOPMENT

Not applicable.

BACKGROUND

This section of this document introduces information about and/or from the art that may provide context for or be related to the subject matter described herein and/or claimed below. It provides background information to facilitate a better understanding of the various aspects of the present disclosure. It is a discussion of "related" art. That such art is related in no way implies that it is also "prior" art. The related art may or may not be prior art. The discussion in this section of this document is to be read in this light, and not as admissions of prior art.

The field of cytometry involves the measurement of properties of individual biological cells suspended in a liquid medium. Cytometry uses optical properties of the cells themselves, such as light scattering properties, to identify and classify individual cells in a sample or fluorescent labels selectively attached to certain cells to further identify cells. Where fluorescent labels are used, multiple fluorescent labels may be used simultaneously, where each label can be distinguished by the spectral characteristics (color) of the light emitted or fluoresced by that label as well as the absorption and excitation of the label by illumination at different wavelengths.

Cytometry sometimes includes the measurement of a number of parameters of each cell in the sample. These parameters may include the size, morphology, cell type, health status (live or dead), deoxyribonucleic acid ("DNA") content, and presence or absence of certain proteins or other molecules on the surface of the cells. A test may count the number of each type of cell in the sample, assay continuously variable properties of the cells in the sample, or do some combination of these types of tests. These are common examples and still other types of tests or analyses may be performed.

Another method of assaying biological content of a sample, termed here "binding assays", uses microspheres made of polystyrene or other materials to capture and detect proteins or other biologically active molecules in a sample. Instead of measuring properties of individual cells, the microspheres are used to detect the presence or absence of biologically active compounds in the liquid sample. Capture molecules such as antibodies or nucleic acid sequences are attached to the outer surface of the microspheres, which then "capture" the target biologically active compound. The presence of the target compound in the sample may then be indicated using fluorescent labels which also bind to the target analyte, so that the microspheres indicate the presence and quantity of the analyte in the sample by the degree to which material bound to the surface of the microsphere fluoresces. Microsphere assays are able to identify proteins, compounds such as drugs of abuse, and specific nucleic acid sequences that may be present in the sample.

Flow cytometry is a technique within the field of cytometry that uses specially designed optically clear channels to present the particles (e.g., cells) in the sample one at a time to an optical system for measurement. The cells are typically illuminated by one or more focused lasers that illuminate only one cell at a time. The illumination may also be performed with other devices such as light emitting diodes (LEDs), are lamps, or other light sources.

Flow cytometry is an efficient means of evaluating a large number of cells in a sample since the time to measure each individual particle is on the order of a few microseconds. The properties that are typically recorded for each cell include forward scattered light, side scattered light, backscattered light, and one or more colors of fluorescence used to identify the previously referenced fluorescent labels. A flow cytometer might use one, two, or more lasers to collect the desired number of measurements for each particle or cell in the sample.

Flow cytometry suffers a number of drawbacks. One drawback of flow cytometry results from measuring particles sequentially. In order to measure a large number of particles sequentially in a short period of time, the time allowed to measure each individual particle is also short. A second drawback results from the method of illumination typically employed in flow cytometers. In order to provide highly uniform illumination to each particle, whose position within the sample may vary from particle to particle, a field of illumination substantially larger than the particle is used. Typically, an illumination field ten times the diameter of each particle or greater is used illuminate each particle that only varies by a few percent. Consequently, flow cytometers are only able to use a small percentage of the illumination to analyze each particle. Because the illumination source is many times brighter than what is needed to illuminate a particle, the amount of stray light in the optical system is also much higher than desirable. Excess stray light interferes with the flow cytometer's ability to detect very weakly fluorescent particles.

Scanning cytometry, or laser-scanning cytometry, uses a microscope equipped with an optical scanning system to analyze and measure a number of cells or microspheres presented, for example, on a microscope slide for analysis. (Other presentation methods may also be used.) The samples are typically static; that is to say that particles being analyzed are spread out over a flat surface while being analyzed, and the optical system scans across the surface to evaluate the individual particles. Alternately, the slide holding the particles may be translated using a motorized stage beneath a fixed optical analysis system. Like a flow cytometer, a scanning cytometer is able to measure multiple fluorescence and light-scattering properties simultaneously.

Scanning cytometers address the illumination issues of flow cytometers by only illuminating the particle being analyzed with a focused light source (typically a laser).

These instruments also can use lower power illumination sources and have substantially less stray light than flow cytometers.

Whereas a flow cytometer is able to measure an arbitrarily large number of particles for any sample, a scanning cytometer is typically limited by the area the machine can analyze (i.e., the field of view of the microscope). In order to enlarge the surface on which the particles are held, thereby increasing the number of particles that may be measured, scanning cytometers use precise translation stages that can move the surface through the field of view. This method of scanning increases the cost of the equipment and involves a long analysis time during which the scanning occurs.

SUMMARY

In a first aspect, the subject matter claimed below includes an optical analysis apparatus, comprising: a sample delivery system from which a liquid sample may be delivered in operation; a flow cell defining a channel through which, in operation, the delivered liquid sample may flow at a controllable rate, the channel including an optical analysis region; an illumination source focused on a portion of the optical analysis region that, in operation, illuminates a single particle at a time in a stream of the sample wider than the single particle; a detector that, in operation, detects light resulting from the illumination of the sample and outputting a signal representative of the detected light; and an analysis system receiving the representative signal.

In a second aspect, the subject matter claimed below includes an optical analysis method, comprising: flowing a sample stream containing a plurality of particles through an optical analysis region; illuminating each particle one particle at a time as the particle passes through a portion of the optical analysis region, the optical analysis region being wider than the illuminated particle; detecting light emanating from the illuminated particle; generating an image of the detected light; and analyzing the image to determine selected attributes of the illuminated particle.

The above paragraph presents a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The subject matter claimed below and disclosed herein may be understood by reference to the following description taken in conjunction with the accompanying drawings, in which like reference numerals identify like elements.

Figure 1:
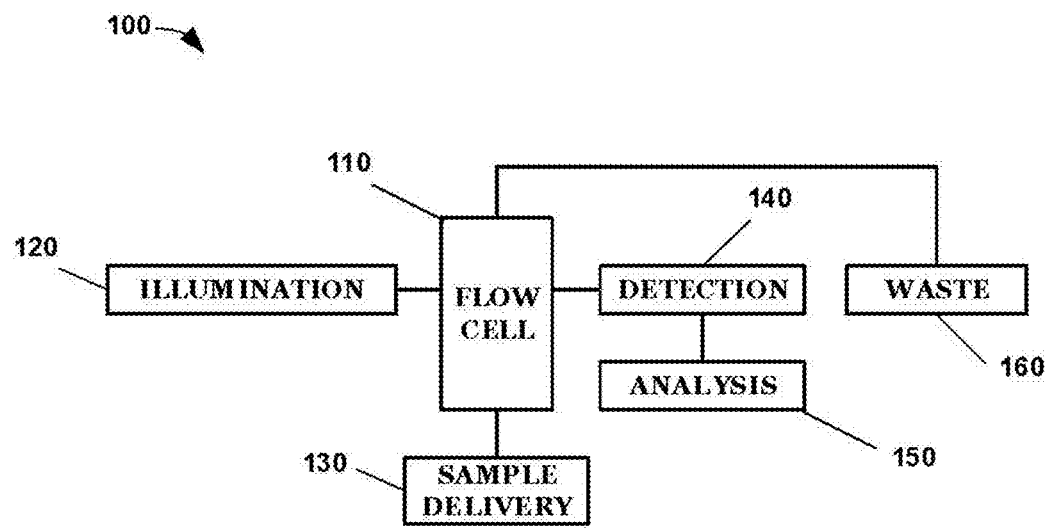
FIG. 1 diagrams one embodiment of a liquid sample handling system that presents particles for optical analysis in one particular embodiment.

While the disclosed technique is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions will be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The present disclosure pertains to a method and apparatus for analyzing particles suspended in a liquid medium (i.e., a sample) by optical measurement of the fluorescence, and/or light-scattering, and/or other optical properties of the individual particles in the sample. More specifically, the disclosure relates to a system that scans the liquid sample with one or more illumination sources and simultaneously records one or more components of scattered light and/or fluorescent light from each particle suspended in the liquid medium while the sample flows through an optically clear flow cell. The method of illuminating the sample and collecting and measuring the light emitted, and/or fluoresced, and/or scattered from each particle permits rapid, sensitive and accurate analysis of a large number of particles in a short time.

The method of analyzing particles suspended in a liquid medium generally including a means of presenting the liquid sample to an optical system for analysis. The liquid handling system may include an optically clear channel designed to move the sample through the optical analysis system so that the particles in the sample move in a substantially flat plane and are able to be illuminated and imaged individually. In this context, "substantially flat plane" means that the plane geometry is such that each particle in the sample lies within the depth of field of the object plane of the optical analysis system The optical analysis may include a device that scans one or more light sources such as lasers across the plane that the particles in the sample traverse, while simultaneously recording one or more scattered light properties and/or one or more fluorescent properties of each particle. The particles in the sample may be biological cells, microspheres, or other particles. The analysis of each particle may take place substantially instantaneously in real-time or near real-time in some embodiments. In this context, "substantially instantaneously" means during the time the particle passes through the optically clear channel of the optical analysis region. The analysis system may also record data from the particles either as a series of images or video which can be archived in a data storage system and/or further analyzed at a later time.

The optical analysis system may comprise a confocal optical system where an objective lens is used both to focus the illumination sources on the particle and to image light scattered and/or emitted and/or fluoresced from the particles onto one or more detectors. The detectors may be photodiodes, photomultipliers, charge-coupled devices ("CCDs"), or other optical sensors. The illumination sources may be focused to areas sized to illuminate only one particle at a time, and the lenses and apertures in the optical analysis system may be designed to spatially filter out stray light which might otherwise interfere with analysis of the particle.

The illumination sources may be focused to the same area or they may be separated in space to enable sequential excitation of each particle by each illumination source. In the case where the illumination sources are focused on different locations within the sample, scattered light and fluorescent light emitted from the particle corresponding to each illumination source would be simultaneously focused on detectors equipped to detect scattered light and fluorescent light pertaining to that illumination source.

In some embodiments, a confocal design may also include an aperture or mask placed in an image plane of the objective lens to spatially filter light from points other than the focal point of the objective. The confocal design may also include optical elements placed after the aperture to focus the light passing through the aperture onto the photodetectors at a magnification suitable to match the size of the image of the sample to the sensitized area of the photodetectors.

Turning now to FIG. 1, one embodiment of an apparatus too for analyzing particles suspended in a liquid medium (i.e., a sample) by optical measurement of the optical properties of the individual particles in the sample is shown. The apparatus too includes a set of systems, each variously handling assigned tasks related to the overall effort. These pieces include a flow cell 110, an illumination system 120, a sample delivery system 130, a detection system 140, an analysis system 150, and a waste system 160.

Figure 2:
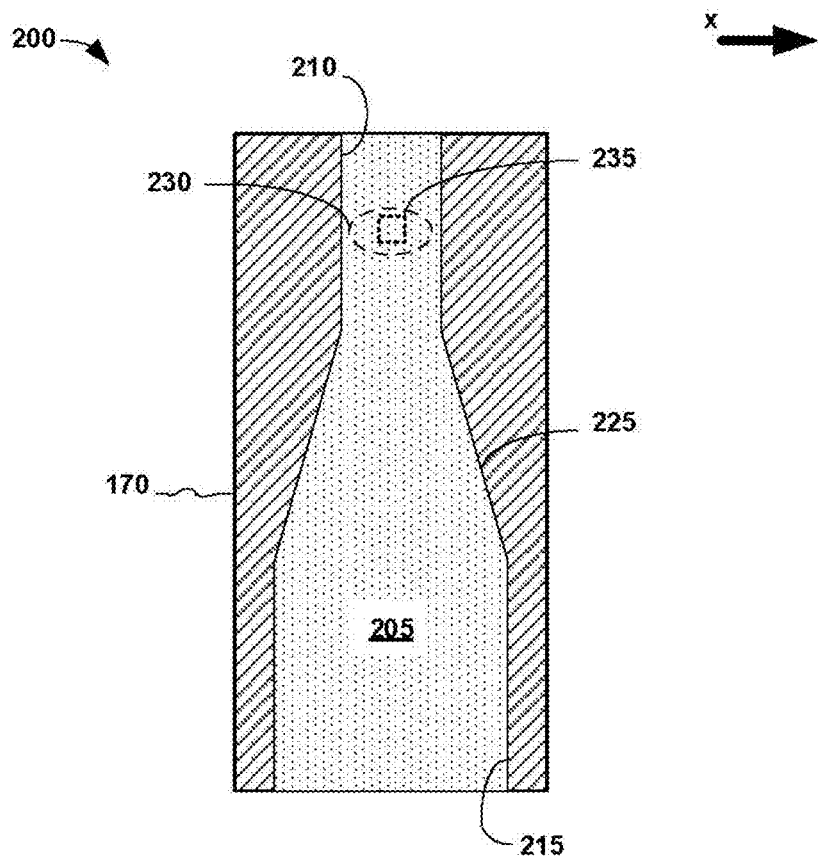
FIG. 2 is a partial cross-sectional view of one embodiment of a portion of a flow cell such as may be used to position a sample for optical analysis in one or more embodiments.

FIG. 2 depicts one particular embodiment of a portion 200 of the flow cell 110 with a sample 205 already introduced. A sample needle (not shown) introduces the sample 205 into the channel 210 defined by the flow cell 110. In this illustration, the flow cell 110 is wider at the point where sample 205 is injected to define a chamber 215 that narrows to a channel 210 where the sample is analyzed. The narrowing forms a throat 225 between the chamber 205 and the channel 210 where the optical analysis region 230 is located. This geometry reduces the size of the channel 210 as the sample 205 flows through an optical analysis region 230. At least the channel 210 is "optically clear" in the sense that the materials of the flow cell 110 that define the channel 210 are translucent to the illumination emanating from the illumination system 120. Thus, in this sense, the channel 210 is an "optically clear channel".

The channel 210 is dimensioned at the optical analysis region 230 in width (in the drawings, along the x axis) so that individual target particles (not shown) in the sample 205 are able to be viewed individually as they pass through the optical analysis region 230. Thus, the precise dimension in terms of width may vary depending upon the size of the target particle being analyzed and the rate at which sample is passed through the system in a manner that will become apparent to those in the art having the benefit of this disclosure. In one particular embodiment, the flow dimensions of the channel 210 may be approximately 100 microns depth (in the drawings, the y direction) and 5 mm width, where the sample would occupy a 1 mm portion 235 of the region 230 within the center of the channel 210.

Figure 3:
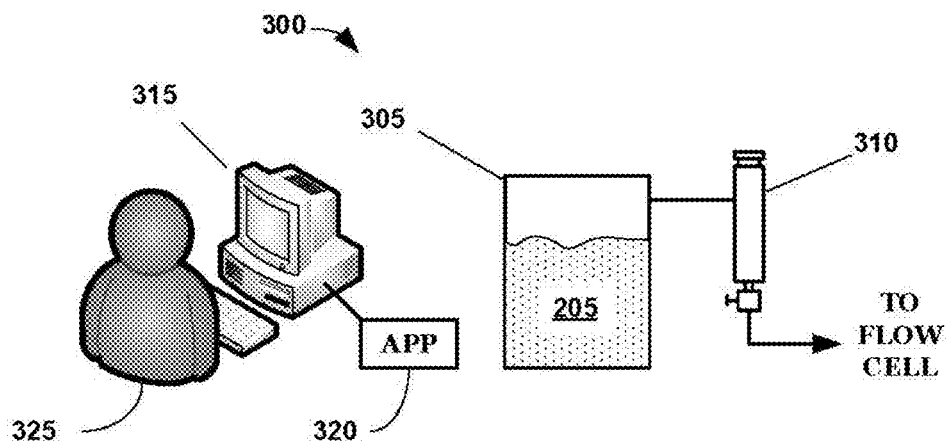
FIG. 3 conceptually illustrates a sample delivery system in one particular embodiment.

Turning now to FIG. 3, one particular embodiment of the sample delivery system 130 of FIG. 1 is shown. The sample delivery system 300 includes a sample reservoir 305 and a pump 310 to provide a motive force to the stored sample 205 and deliver it to the flow cell 110, shown in FIG. 1. The pump 310 in the illustrated embodiment is a syringe pump, but other suitable pumps known to the art may be used in alternative embodiments. The sample delivery system 300 also includes a computing apparatus 315 on which an application 320 resides. A user 325 may control the delivery of the sample 205 from the sample delivery system 300 using the application 320.

Figure 4:
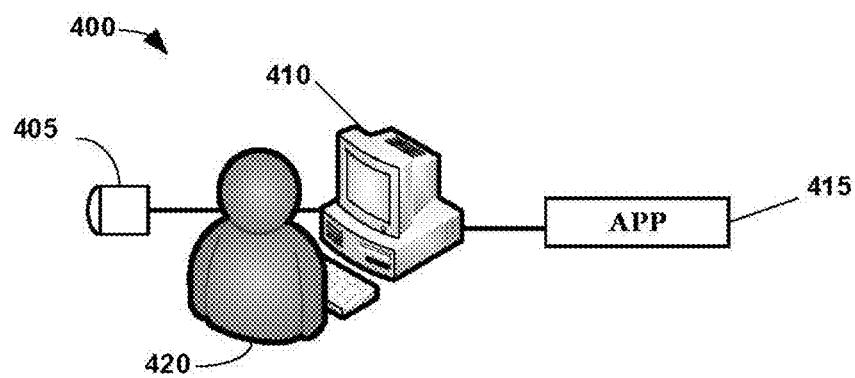
FIG. 4 conceptually illustrates an illumination system in one particular embodiment.

FIG. 4 illustrates one particular embodiment of the illumination system 120. The illumination system 400 includes an illumination source 405, and a computing apparatus 410 on which resides an application 415. A user 420 may control the operation of the illumination system 400 through the application 415. In this embodiment, the illumination source 405 is a laser but may implemented in a wide variety of technologies as discussed above. Many embodiments may include multiple illumination sources 405, such as multiple lasers or multiple LEDs. Still other embodiments may include not only multiple illumination sources 405, but may do so using different technologies. For example, an embodiment (not shown) may employ one or more lasers and one or more LEDs. Furthermore, some embodiments may scan the illumination across a sample whereas others may "flash" the illumination across the sample. In this particular context, "flash" means to illuminate without scanning or otherwise moving the illumination source 405.

Figure 5:
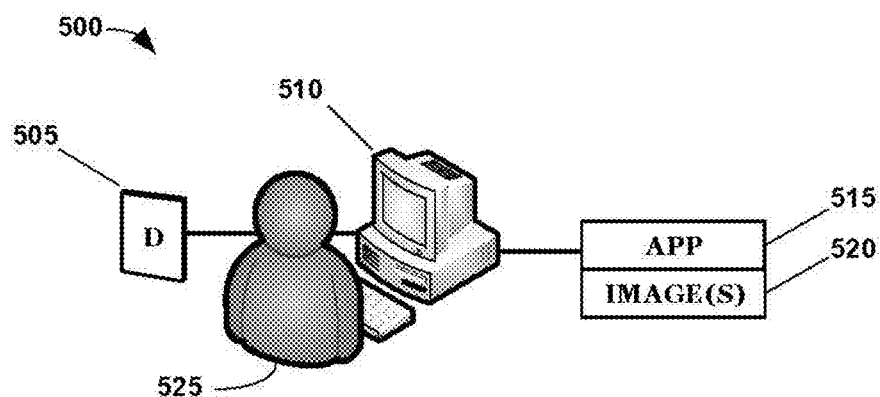
FIG. 5 conceptually illustrates an analysis system in one particular embodiment.

Some embodiments may combine the detection system 140 and the analysis system 150 of FIG. 1. FIG. 5 illustrates one such embodiment. The detection and analysis system 500 shown in FIG. 5 includes at least one detector 505 and a computing apparatus 510. Although not shown in FIG. 5, there will generally be an optical filter placed in the optical path of each detector 505 to make the detector selectively responsive to one region of the electromagnetic spectrum corresponding to the emitted, scattered, or fluorescent light signal being detected. The detector 505 may be, for example, a photodiode or an array of photodiodes chosen for their ability to detect the emitted light at the frequency of interest. Some embodiments may use multiple detectors 505. The detector 505 captures images 520 of the light emitted/ fluoresced/scattered as discussed further below. The images 52o are then stored on the computing apparatus 510. An application 515 resides on the computing apparatus 51o by which a user 525 may control the capture and analysis. The application 515 also performs the analysis under the direction of the user 525.

In some embodiments, the images may be captured from a CCD or CMOS array of pixels such as is disclosed below capturing an image that is digitized and then transferred to the computer. In a scanning system, a detector such as a photodiode would generate a signal that would be digitized at a high rate (e.g., 10 MHz). The data from the detector would be transferred to the computer, then the application would build an image by determining from where in the scan the signal came. The resulting image would be two-dimensional ("2D"), where one dimension would correspond to the scan angle and the other would correspond to the direction of travel of sample through the system. These two dimensions would be orthogonal to each other. The image could also be built by a processor external to the application, such as a digital signal processor ("DSP"), to enable faster processing and better use of bandwidth between the computing apparatus and the other elements of the system.

Figure 6:
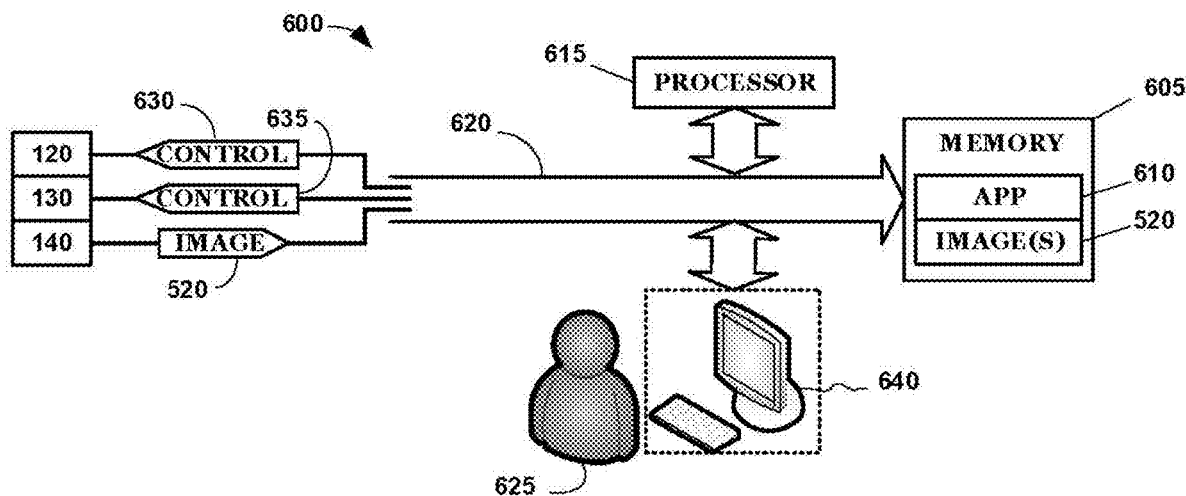
FIG. 6 depicts selected aspects of a hardware and software architecture of a computing apparatus in one particular embodiment.

Those in the art having the benefit of this disclosure will appreciate that some embodiments may combine the functionality of the applications 320, 415, and 515, as well as the computing apparatus 315, 410, 510 into a single application running on a single computing apparatus operated by a single user. One such embodiment is illustrated in FIG. 6. The computing apparatus 600 includes a memory 605 on which an application 610 resides. The memory 605 may include a hard disk and/or random access memory ("RAM") and/or removable storage such as a floppy magnetic disk or an optical disk, each of which is not separately shown. The apparatus also includes a processor 615 and a bus system 620. The processor 615 and bus system 620 may be implemented using any suitable technology known to the art.

The application 610 may be invoked upon power up, reset, or both, or even upon command of the user 625. The application 610, when invoked, performs the method of the presently disclosed technique as will be discussed in greater detail below. In general, the application 610 generates control signals 630, 635 to the illumination and sample delivery systems 120, 130 and receives the images 520 from the detector 505. The images 520 are, at this point, ordered sets of data that may subsequently be rendered for human perception on the display 640 or hard copy printouts (not shown). The rendering may also be performed by the application 610 or by some other kind of commercially available imaging software.

Some portions of the detailed descriptions herein are presented in terms of a software implemented process involving symbolic representations of operations on data bits within a memory in a computing system or a computing device. These descriptions and representations are the means used by those in the art to most effectively convey the substance of their work to others skilled in the art. The process and operation require physical manipulations of physical quantities that will physically transform the particular machine or system on which the manipulations are performed or on which the results are stored. Usually, though not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated or otherwise as may be apparent, throughout the present disclosure, these descriptions refer to the action and processes of an electronic device, that manipulates and transforms data represented as physical (electronic, magnetic, or optical) quantities within some electronic device's storage into other data similarly represented as physical quantities within the storage, or in transmission or display devices. Exemplary of the terms denoting such a description are, without limitation, the terms "processing," "computing," "calculating," "determining," "displaying," and the like.

Furthermore, the execution of the software's functionality transforms the computing apparatus on which it is performed. For example, acquisition of data will physically alter the content of the storage, as will subsequent processing of that data. The physical alteration is a "physical transformation" in that it changes the physical state of the storage for the computing apparatus.

Note also that the software implemented aspects of the invention are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The invention is not limited by these aspects of any given implementation.

In some embodiments, various combinations of all or portions of operations as described by a computing apparatus readable medium having a set of instructions stored therein, are performed by execution and/or interpretation of one or more program instructions, by interpretation and/or compiling of one or more source and/or script language statements, or by execution of binary instructions produced by compiling, translating, and/or interpreting information expressed in programming and/or scripting language statements. The statements are compatible with any standard programming or scripting language (such as C, C++, Fortran, Pascal, Ada, Java, VBscript, and Shell).

One or more of the program instructions, the language statements, or the binary instructions, are optionally stored on one or more computer readable storage medium elements. In various embodiments some, all, or various portions of the program instructions are realized as one or more functions, routines, sub-routines, in-line routines, procedures, macros, or portions thereof. Thus, the functionality of the application 610 may be realized in other types of program constructs besides an application.

It will be understood that many variations in construction, arrangement, and use are possible consistent with the description, and are within the scope of the claims below. For example, the order and arrangement of flowchart and flow diagram process, action, and function elements are variable according to various embodiments. Also, unless specifically stated to the contrary, value ranges specified, maximum and minimum values used, or other particular specifications (such as flash memory technology types and the number of entries or stages in registers and buffers), are merely those of the described embodiments, are expected to track improvements and changes in implementation technology, and should not be construed as limitations.

Functionally equivalent techniques known in the art are employable instead of those described to implement various components, sub-systems, operations, functions, routines, sub-routines, in-line routines, procedures, macros, or portions thereof. It is also understood that many functional aspects of embodiments are realizable selectively in either hardware (e.g., generally dedicated circuitry) or software (e.g., via some manner of programmed controller or processor), as a function of embodiment dependent design constraints and technology trends of faster processing (facilitating migration of functions previously in hardware into software) and higher integration density (facilitating migration of functions previously in software into hardware). Specific variations in various embodiments include, but are not limited to: use of different operating systems and other system software; use of different interface standards, network protocols, or communication links; and other variations to be expected when implementing the concepts described herein in accordance with the unique engineering and business constraints of a particular application.

Figure 7:
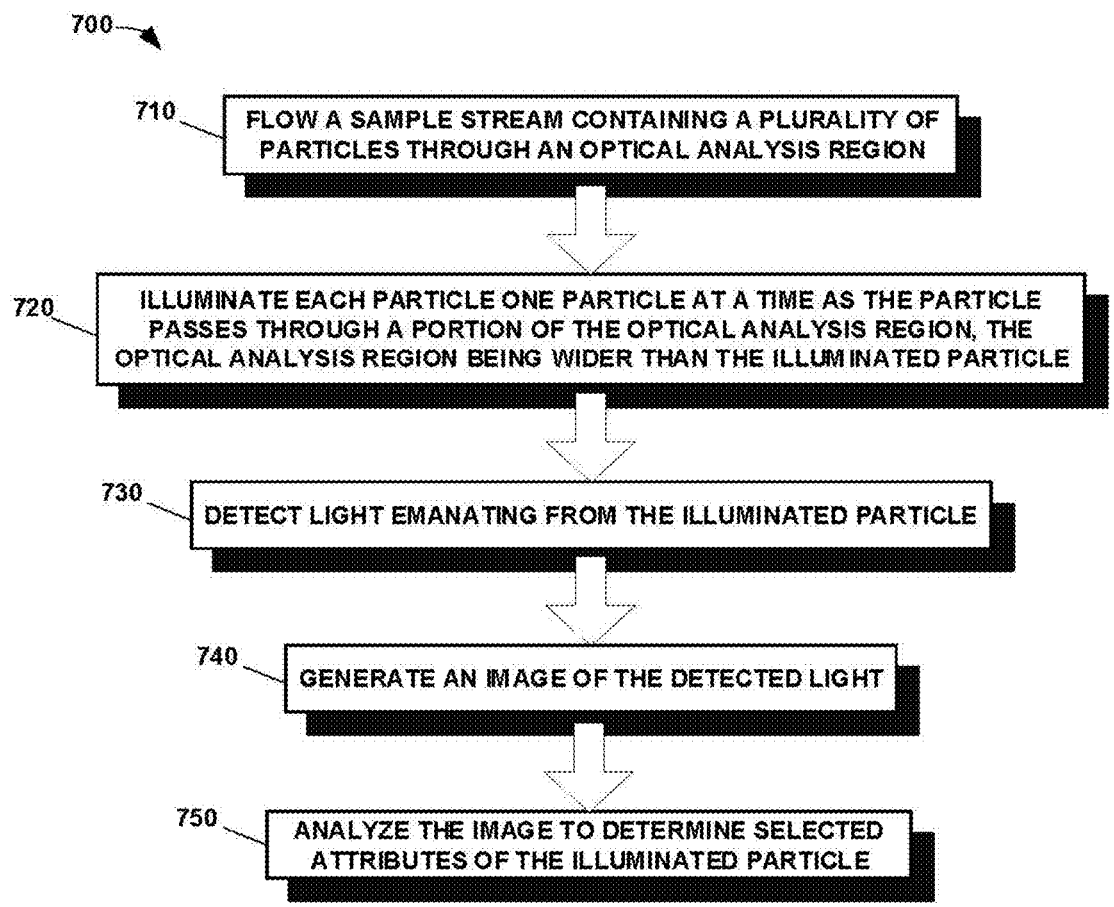
FIG. 7 illustrates a method in accordance with one particular embodiment.

Returning now to FIG. 6, the application 610, when invoked, performs the optical analysis method illustrated in FIG. 7. The method 70o begins by flowing (at 710) a sample stream (e.g., the sample 205) containing a plurality of particles through an optical analysis region (e.g., the optical analysis region 230). It then illuminates (at 720) each particle one particle at a time as the particle passes through a portion (e.g., the portion 235) of the optical analysis region, the optical analysis region being wider than the illuminated particle. The light emanating from the illuminated particle is then detected (at 730).

An image is generated from the detected light (at 740). Where the system includes more than one detector, the data would include an image pertaining to each detector. The multiple images would be registered to one another so that the different scatter and fluorescence signals generated by each detector about each particle could be compiled into one set of measurements including a measurement of each data parameter for each particle. The image is then analyzed (at 740) to determine selected attributes of the scanned particle.

In the optical analysis apparatus too of FIG. 1, the sample 205 is introduced in a manner in which only particles within the optical analysis region 230, shown in FIG. 2, are analyzed. Because the sample 205 occupies the entire width of the channel 210 of the flow cell 200, any particles flowing outside the optical analysis region 230 would not be analyzed. One embodiment utilizes a "sheath fluid" to address this issue.

Figure 8:
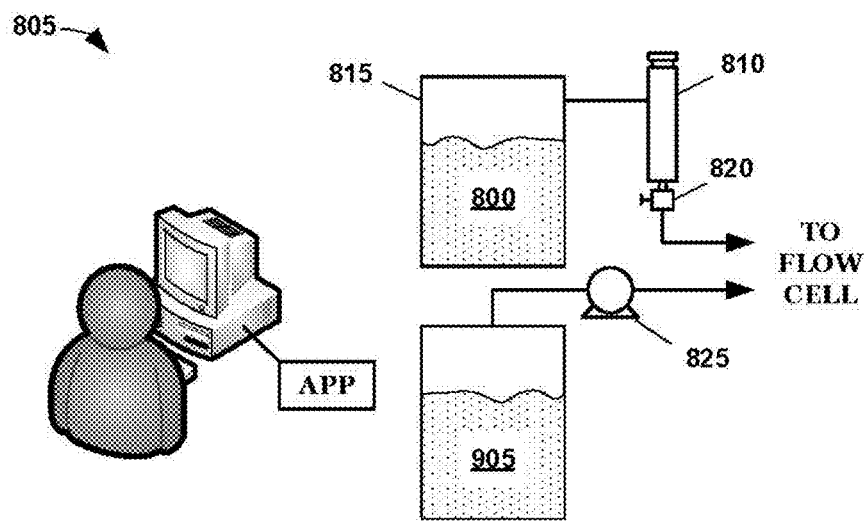
FIG. 8 conceptually illustrates a sample delivery system in one particular embodiment as may be used in conjunction with the flow cell of FIG. 9.
Figure 9:
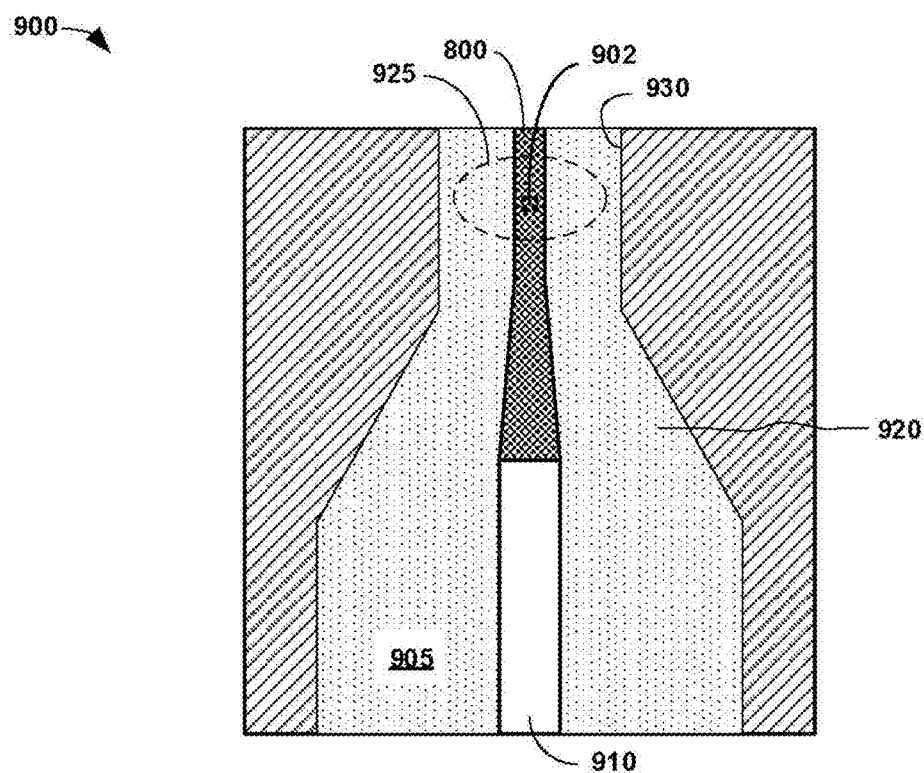
FIG. 9 is a partial cross-sectional view of one embodiment of a flow cell such as may be used to position a sample for optical analysis in one or more embodiments alternative to the one shown in FIG. 2.

In a second embodiment illustrated in FIG. 8 and FIG. 9, a liquid sample 800 shown in FIG. 8 is introduced to an optical analysis system for analysis from a sample delivery system 805. The sample 800 may be a majority of water or saline solution with a number of particles 902, shown in FIG. 9, to be analyzed held in suspension in the sample. A device such as a syringe pump 810 is used to aspirate the sample 800 from an external container 815 such as a vial or other reservoir. A valve 82o connected to the syringe pump 810 is then used to divert the sample to the flow cell for analysis. The sample 800 is injected into a flow cell 900, shown in FIG. 9, from the sample delivery system 805, shown in FIG. 8, for analysis by the optical components of the invention.

Within the flow cell 900, illustrated in FIG. 9, the sample may be surrounded by a buffer of clean fluid such as water or saline solution, which for present purposes shall be called a "sheath fluid" 905. The sheath fluid 905 positions the sample 800 within the center of the flow cell 900 so that it can be analyzed without optical interference from the edges of the flow cell 900. A sheath pump 825, which may be a gear pump or a second syringe pump, supplies sheath fluid 905 to the flow cell 900. The sheath supply rate is varied by the sheath pump 825 to control the speed at which the sheath fluid 905 and sample 800 flow through the flow cell 900. After analysis, the sheath fluid 905 and sample 800 flow out of the flow cell 90o into a waste receptacle (not shown).

Referring now to FIG. 9, a sample needle 910o introduces the sample 800 into the flow cell. The sheath fluid 905 flows around the sample needle 910, carrying the sample 800 through the flow cell 900 for analysis. In this illustration, the flow cell 900 is wider at the point 920 where sample 800 is injected through the sample needle 910 and narrower in the optical analysis region 925 where the sample 800 is illuminated. This geometry reduces the size of the sample 800 as it flows through the optical analysis region 925. The flow cell 900, in this particular embodiment, may have channel dimensions of approximately 100 microns depth and 5 mm width, where the sample 800 would occupy a 1 mm wide region within the center of the channel 930.

Figure 10:
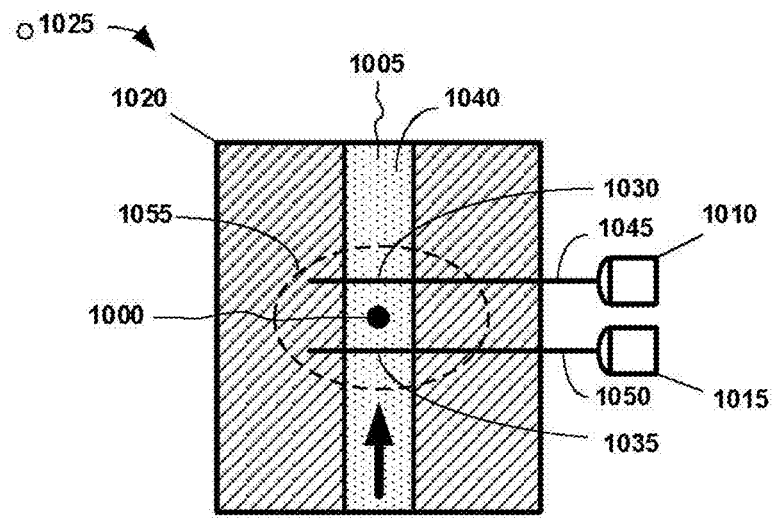
FIG. 10 illustrates one possible embodiment in which particles are scanned in a sample such that each particle may be analyzed individually by multiple illumination sources at distinct times and locations.

FIG. 10 illustrates how particles 1000 in a sample 1005 would be scanned by one or more illumination sources 1010, 1015 as the sample 1005 flows through a flow cell 1020 in one particular embodiment 1025. (Note that there is no sheath fluid in this embodiment.) Each illumination source 1010, 1015 would be focused respectively to a small location 1030, 1035 which may be, for example, 5 microns in width. The illumination sources 1010, 1015 may be co-located or separated in space by a distance such as, for another example, 25 microns.

The focused image of the illumination sources 1010, 1015 may be scanned rapidly across the channel 1040 so that all locations within the channel 1040 receive substantially the same amount of illumination. In the instance where the illumination sources 1010, 1015 are focused on different locations 1030, 1035, each particle 1000 within the sample 1005 would be illuminated sequentially by each illumination source 1010, 1015 and all fluorescent (in this particular embodiment) light and scattered light emanating from the particle in response to the illumination from the different sources 1010, 1015 would occur at different instances in time as well as different physical locations 1030, 1035.

The size of the focused illumination 1045, 1050 from the illumination sources 1010, 1015 may be larger than the particles 1000 being analyzed, smaller than the particles analyzed, or approximately the same size as the particles. Using illumination covering a larger area than a single particle 1000 would result in longer illumination periods for each particle 1000, which would be advantageous for improving the accuracy of the measurements for each particle 1000. Making the illumination 1045, 1050 smaller than the particle size would be advantageous to gain information about the structure of each particle 1000, such as surface texture or presence of internal bodies within a particle, especially if the speed with which particles 1000 flow through the optical analysis region 1055 is slow enough that each particle 1000 is scanned multiple times by the illumination sources 1010, 1015.

The width of the channel 1040 shown in FIG. 10 and the speed with which the sample 1005 moves through the optical analysis region 1055 may be configured in real time by adjusting the rate of injection of the sample 1005 and the rate of injection of sheath fluid (not shown), if used. The direction of flow in FIG. 10 is indicated by the arrow 1060. The width of the area scanned by the optical system may also be configured in real time by adjusting the scanning mechanism (such a galvanometric scanner). Injecting sample 1005 at a higher rate and scanning over a wider optical analysis region 1055 offers the advantage of measuring a larger number of particles in a given period of time. Moving particles 1000 slowly through the system, resulting in more scans for each particle 1000, offers the advantage of more accurate and sensitive measurements of each particle 1000. The optimal configuration for a given sample 1005 should provide a balance of acceptable speed and accuracy.

Figure 11:
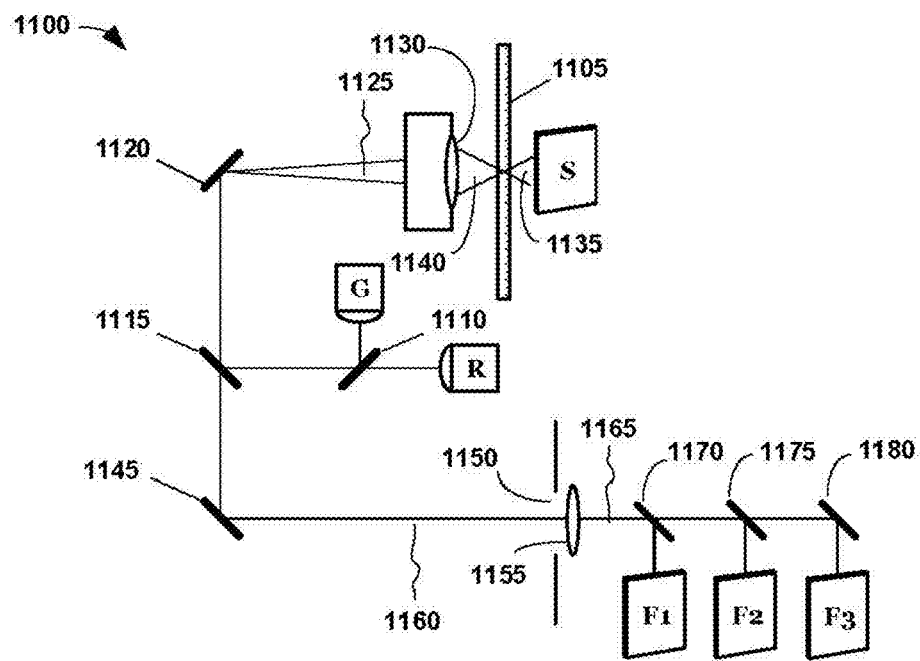
FIG. 11 provides an illustration of an optical system that focuses the illumination sources on the sample and focuses light emanating from particles in the sample on photodetectors in one particular embodiment.

FIG. 11 illustrates the schematic design of one possible embodiment of the optical analysis components of a combined illumination and detection system 1100. The sample 1105 is illuminated in this embodiment by two illumination sources—a red laser R emitting light at approximately 638 nm and a green laser G emitting light at approximately 532 nm. Light from the illumination sources R, G is reflected first by a turning mirror 1110, by a dichroic beamsplitter 1115, and then by a scanning mirror 1120 attached to an optical scanner (not otherwise shown). The optical scanner may incorporate a second turning mirror in some embodiments so that the system can scan in two dimensions or may use only one mirror as shown to scan a linear pattern across the sample 1105. The scanner may also include other optical elements (not shown) such as a scan lens or f-theta lens and a field lens. The light 1125 is then focused onto the sample 1105 within the flow cell (not shown) by an objective lens 1130.

Light 1135 scattered by particles within the sample 1105 is captured by the scattered light detector S as each particle in the sample 1105 is illuminated. The scattered light detector S may incorporate one or more photodetectors, a baffle to deflect a majority of the light flowing through the flow cell from the illumination sources, and one or more optical elements such as lenses used to direct scattered or fluorescent light onto the photodetectors, none of which are shown in Figure ii. The scanning mirror 1120 rotates around one axis orthogonal to the paper so that the focused light 1140 from the illumination sources G, R traverses across the stream of sample 1105 within the flow cell.

In this particular embodiment, the particles have been tagged with "markers" or "labels", as discussed above. The labels are applied to the particles in the sample 1105 prior to their delivery from the delivery system. As described above, the labels are mixed with the particles and each label selectively attaches itself to the particles depending on their biochemical composition. When light of a certain frequency strikes the label, light will fluoresce from the label. From the frequency of the fluoresced light it can be determined what kind of label is present and from the type of label some attribute of the particle can be deduced. The magnitude of the fluorescence signal indicates the quantity of the label attached to the particle. From the magnitude of the fluorescence signal, the concentration of the analyte within the sample can be inferred.

Fluorescent light emitted by the particles is focused by the objective lens 1130, reflected by the scanning mirror 1120 attached to the scanner, passes through the dichroic beamsplitter 1115 that reflects the illumination light, and then is reflected by a second dichroic beamsplitter 1145 onto a confocal aperture 1150. The objective lens 1130 forms an image of the sample 1105 on the plane of the confocal aperture 1150. The confocal aperture 1150 allows light 1160 from the region of the sample 1105 being illuminated to pass through and blocks light 1160 from all other parts of the sample 1105. A lens 1155 focuses the light 1165 from the sample 1105 that passes through the confocal aperture 1150 onto the fluorescence detectors $F_1$, $F_2$, $F_3$. The fluorescence detectors $F_1$, $F_2$, $F_3$. are, in this particular embodiment, implemented in photodetectors. Each photodetector captures a different part of the electromagnetic spectrum corresponding to the fluorescence emission spectrum of one or more fluorescent dyes attached to the particles in the sample 1105.

A dichroic beamsplitter 1170, 1175, 11180 in the optical path of each fluorescence detector $F_1$, $F_2$, $F_3$ reflects light of the desired wavelength range towards that detector $F_1$, $F_2$, $F_3$. So, for example, the dichroic beamsplitter 1170 reflects the light of the frequency sensed by the detector $F_1$ allows light of the frequencies sensed by the detectors $F_2$, $F_3$ to pass. The dichroic beamsplitters 1175, 1180 act in a similar manner relative to the frequencies sensed by the detectors $F_2$, $F_3$ and the spectral content of the rest of the light 1165. In addition, a narrow bandpass filter (not shown) may be placed in the optical path directly in front of one or more of the detectors $F_1$, $F_2$, $F_3$ to reject the maximum amount of light outside the desired region of interest of the spectrum.

By careful positioning of the objective lens 1130, both the illumination sources G, R and the detectors $F_1$, $F_2$, $F_3$ would be focused on the same region of interest within the sample 1105. The optical scanner, such as a resonant galvanometric scanner, piezoelectric scanner, or a spinning mirror, would be used to rapidly scan the focal point of the objective lens 1130 back and forth across the sample. By controlling the speed with which the sheath fluid and sample 1105 flow through the analysis area and the speed with which the scanner traverses the analysis area, the user may ensure that each particle 1000 within the sample 1105 is scanned a minimum number of times for analysis.

For example, the sample 1105 and sheath fluid (if any) may flow through the optical analysis region of the flow cell at a rate of 10 mm per second. The optical scanner may scan the optical analysis region at a rate of 10,000 Hz, and the illumination sources G, R may be focused to a spot, a portion of the optical analysis region 1055, measuring approximately 5 microns in diameter as discussed above relative to FIG. 10.

With this configuration, each line 1045, 1050 that the illumination sources G, R traverse across the optical analysis region 1055 would be separated from the line before it and the line after it by approximately 1 micron. A point within the sample 1105 would be scanned approximately 5 times as it passes through the optical analysis region 1055. By increasing the sheath fluid and sample velocity, each particle 1000 may be scanned fewer times to process more sample 1105 in a given period of time. By slowing the sheath fluid and sample velocity, each particle 1000 may be scanned more times to gain a more accurate reading for each particle 1000 by aggregating a larger amount of scan data together.

The analysis system (not shown) records the time at which each sample signal is detected by the detectors S, $F_1$, $F_2$, $F_3$ as well as the position of the scanner at that time. This method enables the creation of a two-dimensional image of the sample 1005 stream where each optical parameter (scattered light plus each fluorescence measurement) is recorded at each location, measured across the width of the optical analysis region 1055, and time. Image analysis is used to create an estimate, which may be done either substantially in real time (e.g., as each particle travels through the optical analysis region) or after the sample has been analyzed, of the magnitude of the fluorescence and/or scattered signals associated with each particle 1000 in the sample 1005. The profile of the signal recorded as the illumination sources scans across the width of the particle 1000 may also be used to estimate structural characteristics and/or orientation of the particle 1000.

Those in the art having the benefit of this disclosure will appreciate that many variations may be realized in other embodiments within the scope of the claims set forth below. For example, the illumination may be provided by fewer than two or more than two illumination sources. For another example, the illumination may be provided by an illumination source other than a laser, such as a light-emitting diode or an arc lamp.

The scanner may include a mechanism for optically detecting the angular position of the mirror. One such mechanism would include reflecting a reference beam (not shown) onto a detector (not shown) such that the detector issues a pulse signal every time the reference beam crosses the detector. The scanner may scan in two dimensions instead of scanning in a single dimension, producing a sequence of two-dimensional images of the sample as it moves through the optical analysis area.

Some embodiments may sense scattered light from one illumination source or multiple illumination sources. Other embodiments may sense fewer than three or more than three fluorescence signals, each corresponding to a unique region of the electromagnetic spectrum. Still other embodiments may sense light scattered in other directions than light scattered in the direction of illumination, such as back-scattered light or side-scattered light. The detectors in some embodiments may be positioned in such a manner that they are able to sequentially detect light collected as the particle passes through the illumination region of each illumination source so that the instrument may separately detect the fluorescence excited by each illumination source in the range of the electromagnetic spectrum admitted through the optical filters to the detectors.

Embodiments may utilize a diffraction grating and a multi-channel photodetector instead of multiple discrete detectors with discrete filters to capture detailed information about the spectral content of fluorescent light emitted by the particle, enabling the system to discern multiple fluorescent dyes with overlapping but different fluorescence emission spectra. The confocal aperture may also be varied in size to allow more or less light from the sample to reach the detectors.

Note that not all of these variations are necessarily used in all embodiments. Each of these variations may be implemented in permutation to yield a number of different embodiments. Thus, many aspects of any given embodiment will be implementation specific. Several such variations will now be discussed.

Some embodiments may illuminate the stream of particles from the opposite side of the sample as the objective lens. The illumination source may be focused to a very small size on the order of the size of particles being analyzed and rapidly scanned back and forth, or the illumination source may be focused to a line as wide as or wider than the stream of sample being analyzed and with a thickness in the direction of flow of the sample on the order of the size of the particles being analyzed. The flow cell geometry, discussed below, minimizes stray light from the illumination source while also relaxing the alignment tolerances normally experienced with a flow cytometer.

Figure 12:
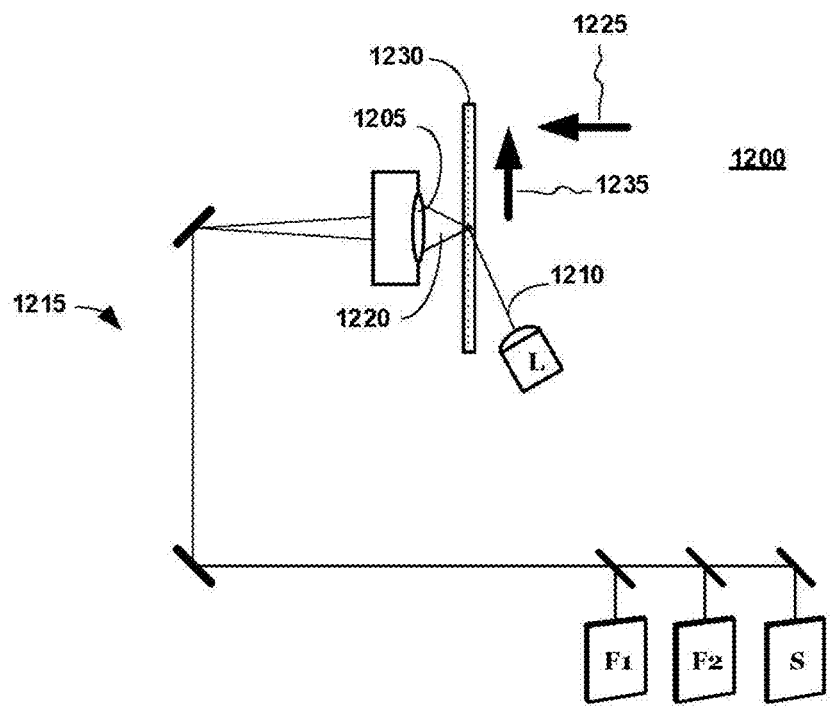
FIG. 12 provides an illustration of an optical system that focuses the illumination sources on the sample and focuses light emanating from particles in the sample on photodetectors in another particular embodiment.
Figure 13:
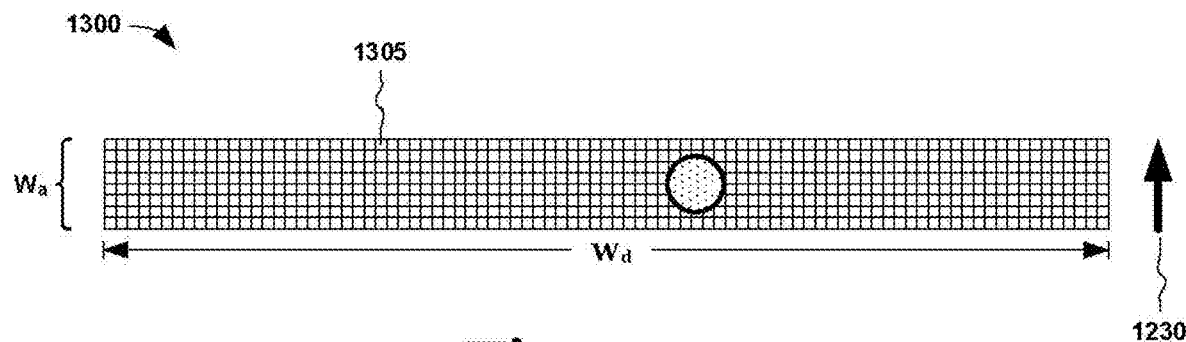
FIG. 13 depicts one embodiment of a detector with an image of a microsphere projected onto the detector by the objective lens.
Figure 14:
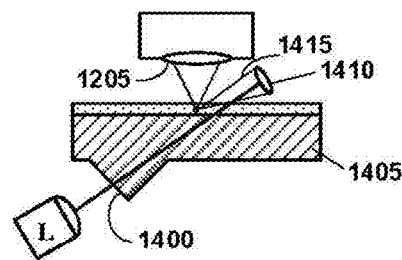
FIG. 14 shows small-angle scatter light exiting the flow cell and being collected by a lens to focus the light onto a detector.

Referring now to FIG. 12-FIG. 14, one or more illumination sources L are located on the side 1200 of the flow cell (not shown) opposite the position of the objective lens 1205 such that the illumination 1210 does not travel through the objective lens 1205 or any of the optical path used to collect scattered and fluorescent light 1220. The light 1220 collected by the objective lens 1205 is not scanned but rather is projected onto one or more stationary detectors $F_1$, $F_2$, S. The stationary detectors $F_1$, $F_2$, S are arrays 1300 of photosensitive elements 1305 (only one indicated), or "pixels", such as charge-coupled devices ("CCDs") or complementary metal oxide semiconductor ("CMOS") as shown in FIG. 13. The array 1300 is sufficiently wide ($W_d$) perpendicular, as indicated by the arrow 1225 in FIG. 12, to the direction of flow of the sample 1230, as indicated by the arrow 1235 in FIG. 12, to image the entire sample 1230 stream contemporaneously.

As shown best in FIG. 14, light 1410 from the illumination source L enters the sample 1230 at a sufficiently small angle with respect to the outside surface 1400 of the flow cell 1405 closest to the objective lens 1205 that substantially all of the light 1220 will be internally reflected after illuminating the sample 1230. The flow cell 1405 may fabricated with a surface 1400 that is approximately perpendicular to the direction of travel of the illumination source L to minimize reflections and scattered light where the illumination enters the flow cell 1405. The flow cell 1405 may incorporate a surface that is perpendicular to the direction of travel of the light from the illumination source and which is located where the light from the illumination source leaves the flow cell after illuminating the sample to facilitate collection of light scattered by the particles at small angles to the direction of travel of the illumination as shown in FIG. 14.

The flow cell 1405 may incorporate an optical element such as a cylindrical lens (not shown) to focus the illumination source L onto the sample 1230 such that the area of sample 1230 illuminated approximately aligns with the area of the sample 1230 imaged onto the one or more detectors (not shown). A lens 1410 may be used to focus light 1415 scattered by the particles 1420 at small angles to the direction of travel of the illumination onto one or more detectors (not shown). In some alternative embodiments, the illumination source L may be focused to a spot with dimensions on the order of the size of the particles being analyzed which is then scanned rapidly back and forth across the sample stream using a scanning device such as a galvanometric scanner, acousto-optic modulator, or rotating mirror.

Other embodiments may include detectors that are multi-pixel arrays 1300 (CMOS sensors, CCD arrays, e.g.) as shown in FIG. 13 and the illumination source L, shown in FIG. 12, is scanned rapidly back and forth across the sample 1230 while the image of the sample stream on the one or more detectors $F_1$, $F_2$, S remains fixed spatially, such that the position of each pixel 1300 in FIG. 13 in each detector $F_1$, $F_2$, S images a fixed position in the sample stream.

More particularly, and referring to FIG. 12, the one or more illumination sources L are scanned back and forth across the sample 1230 while holding the other components of the optical system (detectors, bandpass filters, objective lens, etc.) fixed. The "other components" include, for example, the detectors $F_1$, $F_2$, S, bandpass filters (not shown), the objective lens 1205, etc. Each illumination source L combined with the scanning apparatus (not shown) produces a narrow line of illumination across the width of the sample 1230 similar to that shown in Figure to, and the area of the sample 123o that is so illuminated is imaged onto the one or more detectors $F_1$, $F_2$, S.

The one or more detectors $F_1$, $F_2$, S may comprise an array of photosensitive elements (e.g. a CMOS or CCD array) where the width of the array perpendicular to the direction of flow of the sample stream is substantially as wide as or wider than the image of the sample stream, and where the size of each pixel element is no larger than the image of each particle being analyzed but may be substantially smaller than the size of the image of each particle being analyzed. FIG. 13 depicts one embodiment of a detector with an image 1310 of a microsphere (i.e., one particular embodiment of a particle 1420, in FIG. 14) projected onto the detector by the objective lens The digitization of the image collected by each of the one or more detectors $F_1$, $F_2$, S may be coordinated with the illumination system 120 shown in FIG. 1 that scans the illumination source L across the sample 1230 such that the array 1300 of photosensitive elements 1305 shown in FIG. 13 begins accumulating photoelectrons when the illumination source L begins its traverse across the sample 1230, is integrated for the duration of the time in which the illumination source L traverses across the sample 1230, and is then converted to a digital signal (e.g., image 520 in FIG. 5) immediately after the illumination source L finishes each traverse across the sample 1230 such that each image 520 collected by the one or more detectors 1305 records a single complete scan of the entire sample 1230. The method of digitizing images 52o described previously may be configured such that the integration time for each image 520 is a multiple of the time for the illumination source L to traverse across the sample 1230, such that each image 520 records multiple scans of the sample 123o by the illumination sources L.

Still other embodiments may extend the dynamic range of the measurement of light from each particle by using one or more two-dimensional multi-pixel arrays of photosensitive elements (pixels) which image each particle at different points in time as it travels through the illumination area, and where the amount of illumination each particle receives varies as it travels through the illumination area.

Figure 15:
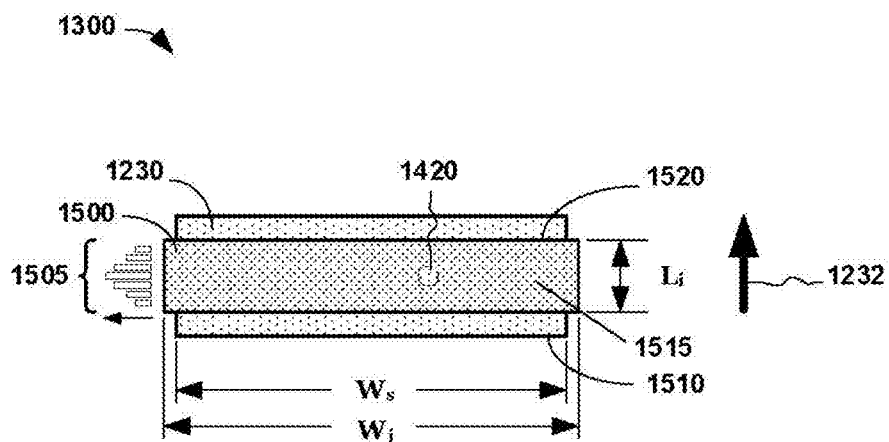
FIG. 15 illustrates an illumination area covering the sample stream and having an intensity that varies along the direction the sample flows through the illumination area.

Referring to FIG. 12 and FIG. 15, the illumination source L produces an area of illumination 1500 which the sample 1230 flows through that is as wide as or wider ($W_i$) than the width of the sample 1230 ($W_s$) and has a length ($I_d$) in the direction of the flow of the sample 1230 (indicated by the arrow 1232) that is a few times the size of a typical particle 1420 being analyzed. For example, if the typical particle 1420 being analyzed has a diameter of 5 microns, the width $W_i$ of the illumination area 1500 in the direction of travel 1232 of the particles 142o may be approximately 50 microns.

The intensity 1505 of the illumination varies as a function of position such that the particle 1420 experiences different levels of illumination as it travels through the illumination area 1500 as is illustrated in FIG. 15. For example, the illumination intensity 1505 might vary according to a Gaussian distribution so that the particle 1420 experiences an increasing level of illumination intensity 1505 as it travels from the first edge 1510 of the illumination area 1500 to the middle 1515 of the illumination area 1500 and then a decreasing level of illumination intensity 1505 as the particle 1420 travels to the second edge 1520 of the illumination area 1500.

Figure 16:
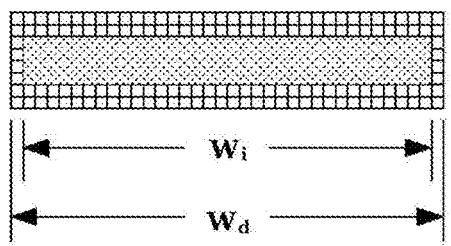
FIG. 16 shows the image of the illumination area projected onto the detector where the illumination area covers multiple pixels in the direction that sample flows through the illumination area.

The sample 1230 is imaged by the objective lens 1205 onto one or more detectors $F_1$, $F_2$, S each including an array 1300 of photosensitive elements (such as a CCD or CMOS sensor), where the width of the array 1300 in the dimension across the sample 1230 is as large as or larger than the width $W_i$ of the image of the sample 1230 and where the width $W_i$ of the detector in the direction of flow 1232 of the sample 1230 is on the order of the size of the image of the sample area illuminated as described above for FIG. 16. The size of the pixels in the detector $F_1$, $F_2$, S is small enough that the image of the sample area covers multiple rows of pixels in the direction of travel 1232 of the particles.

As the particle 1420 travels through the illumination area 1500 and is illuminated by different intensities 1505 of light, multiple recordings of the fluorescent and scattered light from the particle 1420 are recorded. Measurements of the light from the particle 1420 as it travels through the most intense part of the illumination produce the most sensitive measurements of the fluorescent and/or scattered light emitted from the particle 1420 because the intense illumination induces the greatest levels of scattered and fluorescent light to be emitted from the particle 1420.

Particles 1420 that tend to fluoresce very brightly and/or scatter a large portion of the light from the illumination source L may saturate the detector $F_1$, $F_2$, S when the particles 1420 are illuminated by the most intense region of the illumination area 1500. The fluorescence and light scattering properties of those particles 1420 can be measured accurately when the particles 1420 travel through the less intense regions of the illumination area 1500, since both scattered light and fluorescence emissions will be lower when the illumination intensity 1505 is lower and will not saturate the detector $F_1$, $F_2$, S at lower illumination levels.

Still other embodiments may include a two-dimensional scan pattern that improves the consistency of illumination experienced by the particles in the sample. The scanning mechanism scans in two orthogonal dimensions simultaneously: a first dimension X that is perpendicular to the flow of the sample through the optical analysis region and a second dimension Y that is parallel to the flow of particles through the optical analysis region. The illumination area and the area imaged by the objective lens (collectively the area of interest) are scanned in a pattern whereby the scan in the X direction extends from 100%-200% of the width of the sample stream. As the area of interest is scanned through the sample stream in the X direction, the area of interest is scanned in the Y direction at a velocity that matches the velocity of the sample. As the area of interest is scanned outside the sample stream, the area of interest is scanned in the Y direction in the direction opposite to the flow of sample and at a speed greater than the speed of the sample flow such that the total distance traversed by the area of interest in the Y direction during each scan cycle sums to zero.

Figure 17:
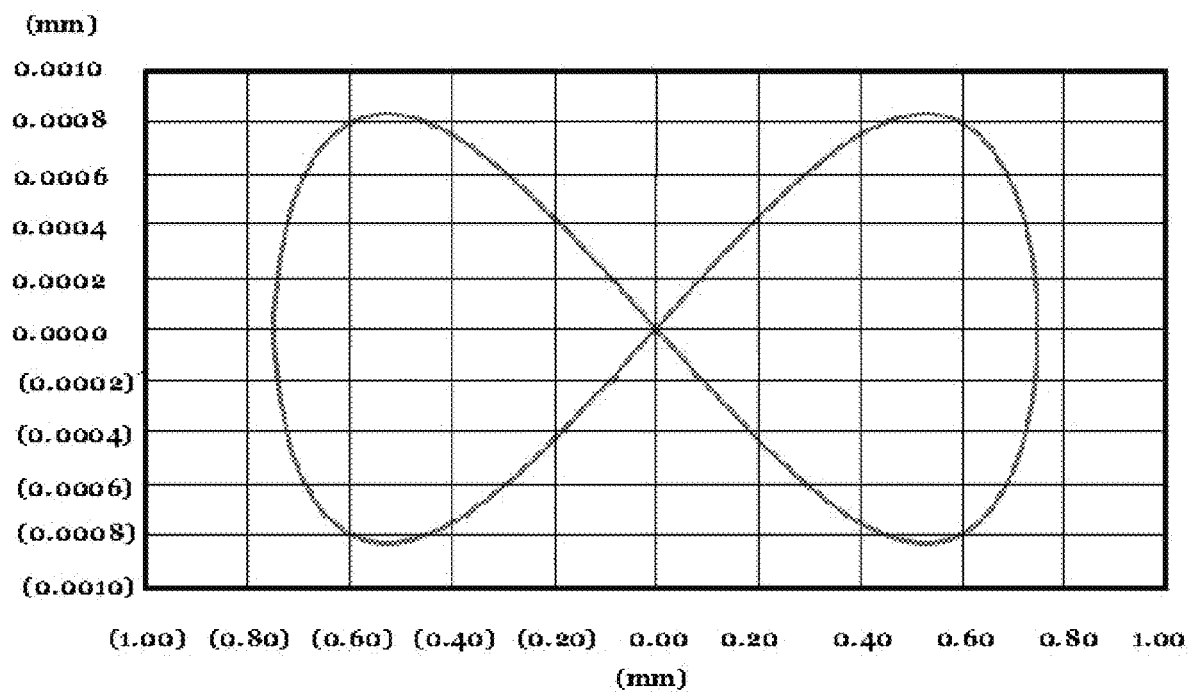
FIG. 17 depicts a lemniscate pattern that may be used as the path of the area of interest in some embodiments.
Figure 18:
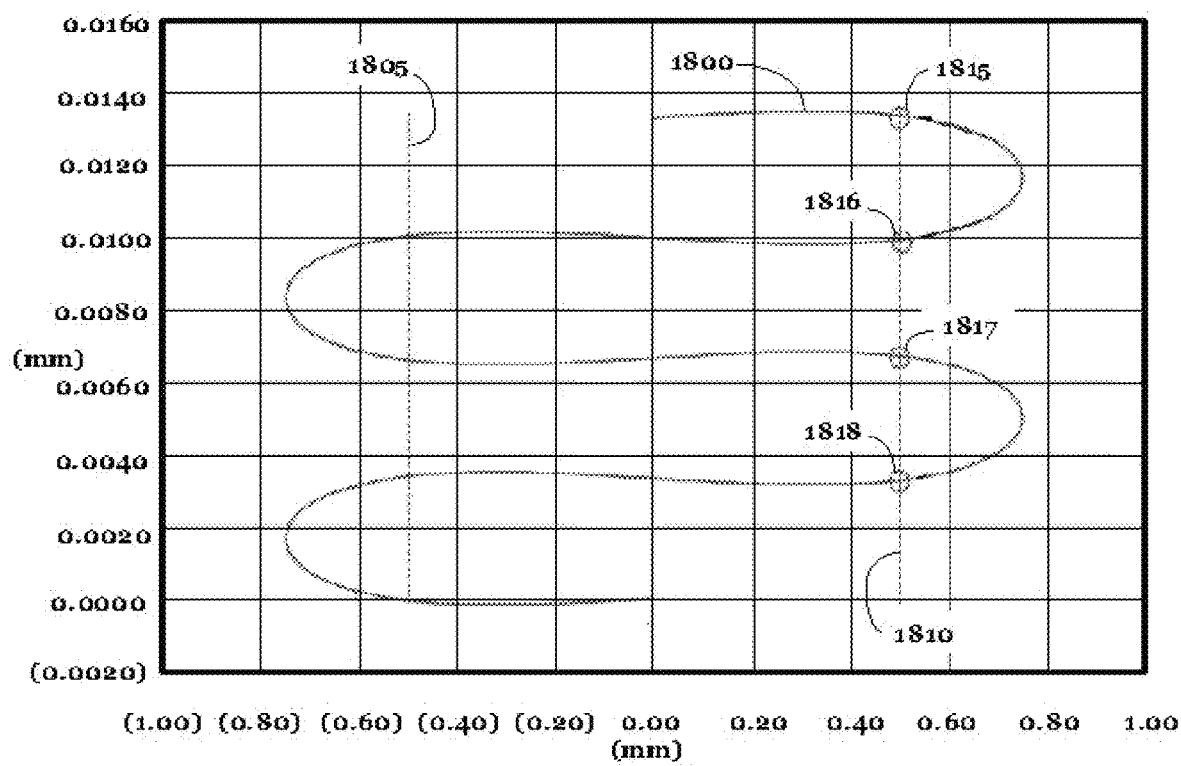
FIG. 18 shows the path of the area of interest from the frame of reference of a particle in the sample stream if the area of interest is steered along a lemniscate pattern as shown in FIG. 15.

One such pattern is a lemniscate of the form $X^4=C^2*(X^2-Y^2)$, shown in FIG. 17, where X is the position of the area of interest in the X direction, Y is the position of the area of interest in the Y direction, and C is a constant. The movement of the area of interest across the sample stream follows a pattern that approximates a square wave in the frame of reference of a particle moving through the system rather than a sine wave. This scan pattern makes the distance between points in the sample stream in successive scans approximately uniform across the entire width of the sample stream (FIG. 18). If the scan follows a simple sinusoidal or triangular wave in one dimension (X) across the sample stream, the area of interest will traverse the center of the sample stream at a regular interval but will traverse the edges of the sample stream at a varying interval as shown in FIG. 19.

Referring to FIG. 18, more particularly, the curve 1800 represents the position of the beam emitted by the light source. The line 1805 represents the left edge and the line 1810 represents the right edge of the sample stream. The area of interest traverses the right edge 1810 of the sample stream at substantially regular intervals when the scan position follows the path described above and shown in FIG. 17. The circles 1815-1818 indicate where the right edge 1810 of the sample stream is illuminated and imaged in successive scans.

Figure 19:
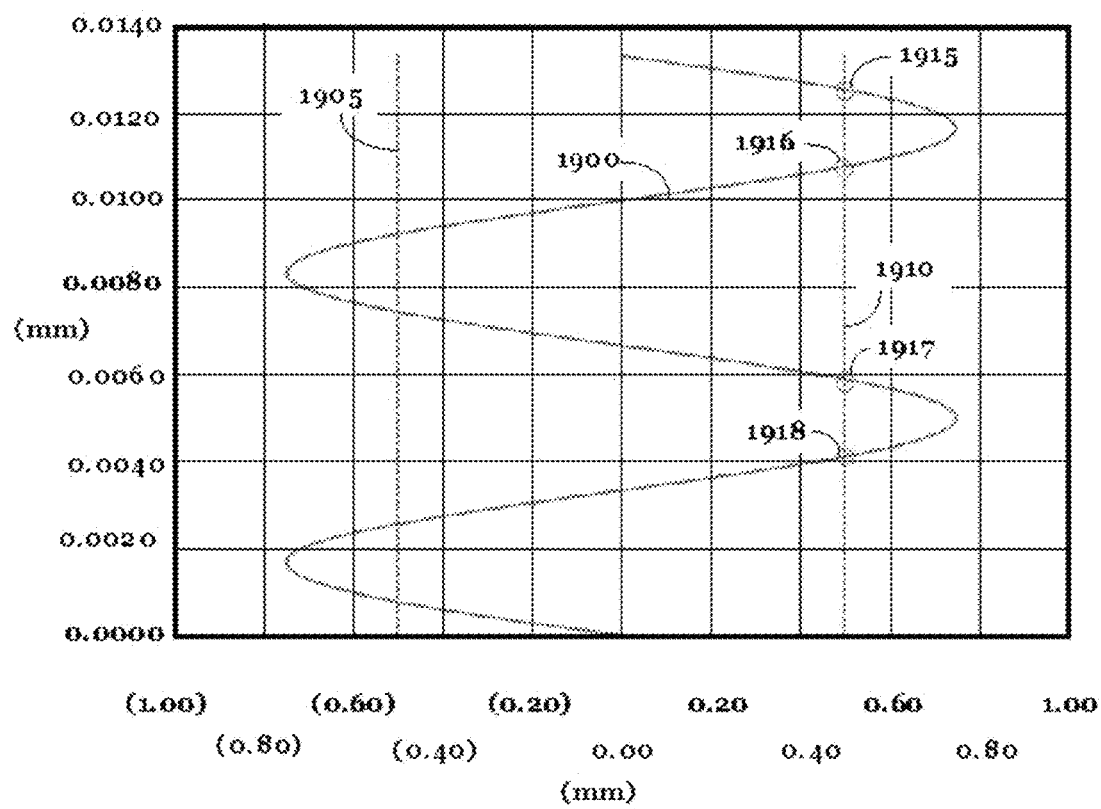
FIG. 19 illustrates the path of the area of interest from the frame of reference of a particle in the sample stream if the area of interest is steered along a sinusoidal path in the X direction and held constant in the Y direction.

Referring to FIG. 19, more particularly, the sinusoidal curve 1900 represents the beam position of the beam emitted by the light source when scanned across the sample area in a linear pattern where the scan angle is a sinusoidal function in time. The line 1905 represents the left edge and the line 1910 represents the right edge of the sample stream. The area of interest traverses the right edge 1910 of the sample stream at irregular intervals when the scan position follows the sinusoidal path described above. The circles 1915-1918 indicate where the right edge 1910 of the sample stream is illuminated and imaged in successive scans.

Still other embodiments may scan two-dimensional areas of sample where the particles are relatively immobile during each scan such that the sample acquisition results in a series of two-dimensional images of the sample. The position of the area of interest in the X direction scans back and forth across the sample stream such that the position of the area of interest scans at a substantially constant speed across the sample speed during each traverse. When the area of interest is scanning over the sample stream, the speed the area of interest moves in the Y direction is approximately equal to the velocity of particles flowing through the illumination area. When the area of interest is scanning outside the sample stream, the speed the area of interest moves in the Y direction is different than the velocity of particles flowing through the sample stream such the subsequent scan will traverse a different position within the sample stream in the Y direction.

After a sufficient number of scans have been acquired to build a two-dimensional image of the dimensions desired by the user, the position of the area of interest in the Y direction resets to the original Y location to begin acquisition of the next 2-dimensional image. This method of scanning the sample stream enables the capture of data at an arbitrary resolution in the X and Y directions for a large range of velocities of sample through the system, and without undesirably high scanning frequencies or high detector sampling frequencies. Scanning at lower scan rates and sampling at lower rates will result in a higher signal-to-noise ratio for the fluorescent and scattered light measurements of each particle.

Figure 20:
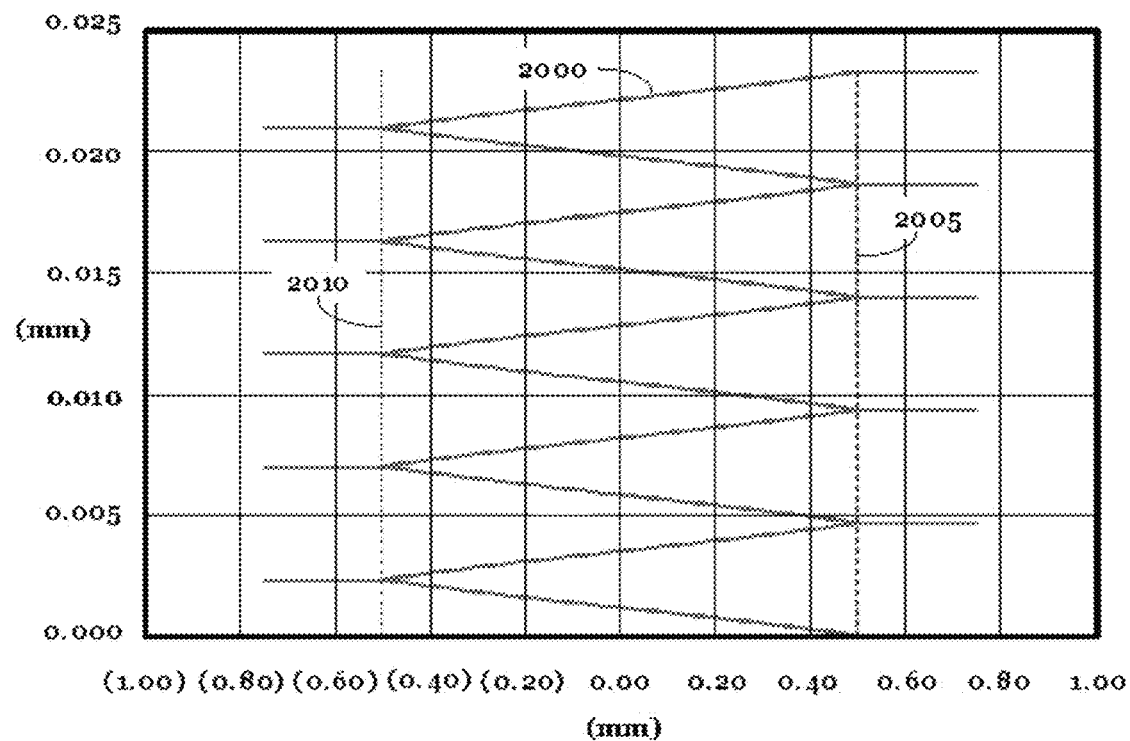
FIG. 20 shows the position of the area of interest relative to the system on one embodiment.

In FIG. 20, the position of the area of interest relative to a fixed frame of reference is shown. In this instance, the position of the area of interest in the X direction follows a sinusoidal pattern 2000 that is 150% the size of the sample stream (right edge 2005 to left edge 2010). The position of the area of interest in the Y direction moves in the same direction and at the same speed as particles in the sample stream when the area of interest scans the sample stream but is held constant in the Y direction when the area of interest scans outside the sample stream.

Figure 21:
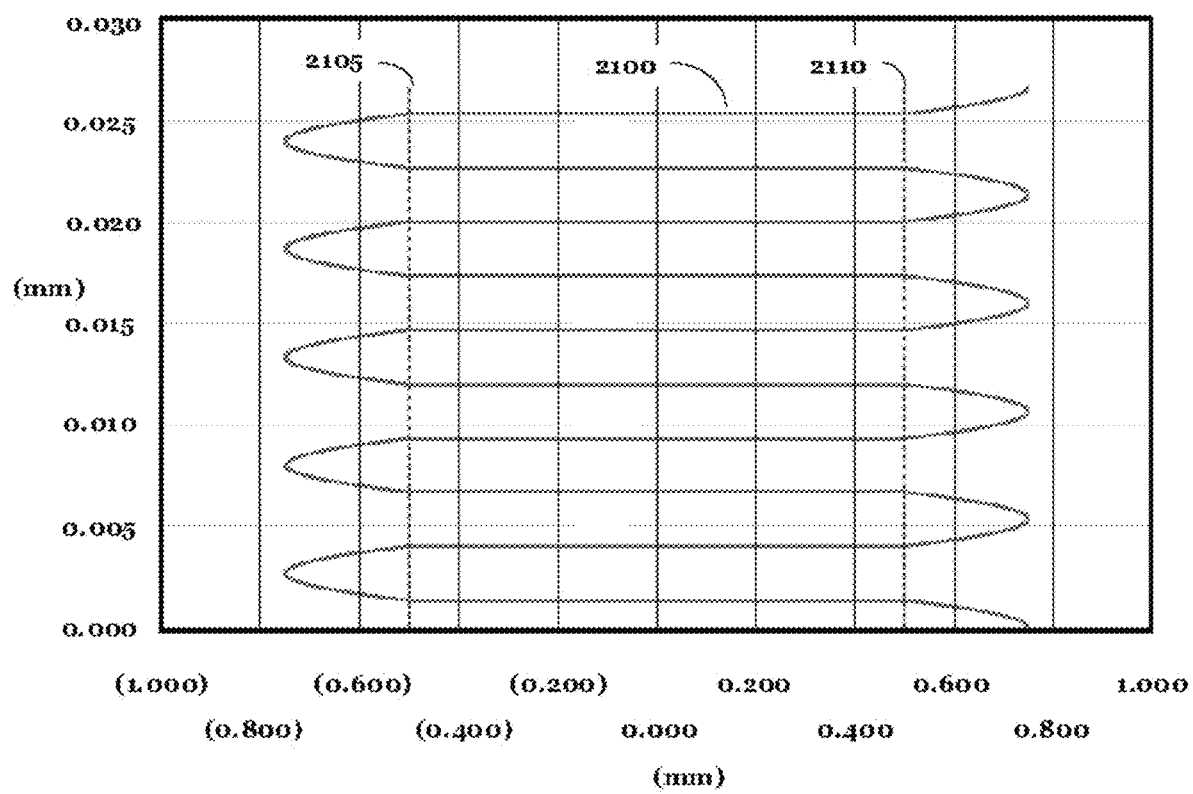
FIG. 21 shows the position of interest relative to the frame of reference of particles moving through the system in one embodiment.

FIG. 21 shows the position of the area of interest from FIG. 20 relative to the frame of reference of particles moving through the system during the acquisition of a 2-dimensional image. The figure does not show the location of the area of interest returning to the start position at the end of a sufficient number of scans to build a complete 2-dimensional image. The area of interest location is represented by the sinusoidal curve 2100 and crosses both the left edge 2105 and the right edge 2110 of the sample stream at regular intervals.

Figure 22:
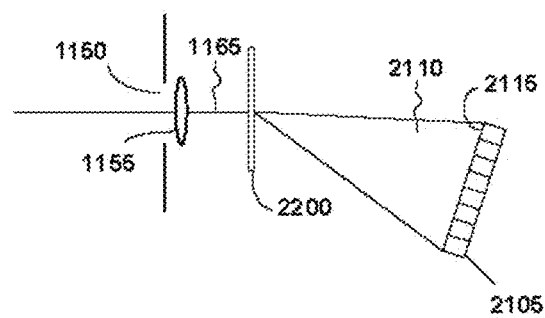
FIG. 22 illustrates how the embodiment of FIG. 11 may be modified to employ a diffraction grating and a multi-component detector.

As noted above, some embodiments may employ a diffraction grating in conjunction with a multi-component detector. FIG. 22 illustrates how the embodiment of FIG. 11 may be modified to employ a diffraction grating 2200 and a multi-component detector 2205. The light 1165 passes through the diffraction grating 2205 which refracts the light 2110 across the surface 2115 whereupon it is detected and the detected signal processed as described above. The multi-component detector 2205 is also a multi-channel detector and may be, for example, a photomultiplier tube. Alternatively, the multi-component detector 2205 may be some alternative technology such as a CCD or CMOS detectors as described above.

Still other embodiments may inject the sample into the flow cell in discrete volumes, each volume separated in time from other volumes injected by a pause during which the volume is scanned. Each volume injected is of sufficient size to approximately fill the imaging area of the flow cell. During each scan, the system raster scans a large area such as a 2 mm×2 mm square. The sample does not flow during the scan, so the particles are substantially motionless (where 'substantially motionless' means that the speed of travel of each particle is much smaller than the speed with which the area of interest scans across the sample) during the scan. Because the sample injection is paused during each scan, the speed with which the sample is scanned may be made faster to obtain higher throughput of sample or slower to obtain better sensitivity. The sample may also be scanned multiple times using different illumination intensity or detector settings to achieve measurements with higher dynamic range and/or increased precision.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What I claim is:

1. An optical analysis apparatus, comprising:
    (a) a sample delivery system from which a liquid sample may be delivered;
    (b) a flow cell defining a channel including an optical analysis region and through which the liquid sample flows;
    (c) an illumination source;
    (d) a controllable moveable illumination scanning mechanism wherein:
        (i) the structured movement traverses and illuminates the optical analysis region in a plurality of directions wherein the light originates from the illumination source;
        (ii) the movement is structured to make a measurement of a particle and generate an image of the particle;
    (e) an objective lens that conveys light from the illumination source to the liquid sample, images light emanating from the illuminated optical analysis region of the liquid sample onto an image plane, and through which light emanating from the sample in response to the illumination is detected;
    (f) a detector to detect light emanating from the sample and collected by the objective lens in response to the illumination of the sample; and
    (g) an aperture placed in an image plane of the objective lens to spatially filter light from points other than the focal plane of the objective lens, which is within the liquid sample flow, before the light reaches the detector.

2. The optical analysis apparatus of claim 1 wherein the movement of the illumination traversing the optical analysis region includes an X vector perpendicular to a direction of the liquid sample flow and a Y vector parallel to the direction of the liquid sample flow and further that a velocity of movement of the Y vector may be substantially equal to a velocity of the liquid sample flow.

3. The optical analysis apparatus of claim 2 wherein the two-dimensional pattern of the traversing optical scanner achieves consistency of illumination.

4. The optical analysis apparatus of claim 1 wherein the extent of the traverse in the X or Y direction or rate of traverse of the optical analysis region can be controlled in real time.

5. The optical analysis apparatus of claim 2 wherein the traversable optical scanner utilizes a lemniscate pattern.

6. The optical analysis apparatus of claim 5 wherein the Y location of the optical scanner is reset after each traverse in the X direction.

7. The optical analysis apparatus of claim 1 wherein the two-dimensional traversing optical scanner achieves multiple two-dimensional images of the sample.

8. The optical analysis apparatus of claim 1 wherein the sample may be illuminated by two illumination sources wherein light from the illumination sources is reflected first by a first dichroic beamsplitter, by a second dichroic beamsplitter, and then by a scanning mirror attached to the optical scanner.

9. The optical analysis apparatus of claim 8 further comprising a scanning mirror rotating on an axis orthogonal to the sample flow direction.

10. The optical analysis apparatus of claim 8 further comprising a second scanning mirror thereby allowing the apparatus to scan in two dimensions.

11. The optical scanner of claim 8 wherein the optical scanner may further comprise a scan lens, f-theta lens or a field lens.

12. An optical analysis apparatus comprising:
    (a) a sample delivery system comprising:
        (i) a delivery component for delivery of a liquid sample;
        (ii) a flow cell component defining a channel to which the liquid sample is delivered;
    (b) combination of an illumination source, moveable scanning mechanism, and an objective lens wherein the illumination source, moveable scanning mechanism and objective lens are structured to illuminate an optical analysis region of the flow cell to make a measurement of a particle and generate an image of the particle; and
    (c) the controllable moveable scanning mechanism further traverses the optical analysis region in a plurality of directions.

13. The optical analysis apparatus of claim 12 wherein the flow control component can control the sample flow rate through the optical analysis region in real time.

14. The optical analysis apparatus of claim 12 wherein the flow control component can control the sample flow rate through the optical analysis region in real time.

15. A method of conducting optical analysis, comprising:
    (a) delivering a sample into a flow cell defining a channel including an optical analysis region and through which the liquid sample flows;
    (b) illuminating the liquid sample with an illumination source and scanning mechanism;
    (c) controlling the moveable illumination scanning mechanism wherein the moveable illumination scanning mechanism traverses the optical analysis region in a plurality of directions;
    (d) creating an image using an objective lens that conveys light from the illumination source to the liquid sample, imaging the light emanating from the illuminated optical analysis region of the liquid sample onto an image plane and through which light emanating from the sample in response to the illumination is detected; and
    (e) utilizing an aperture placed in an image plane of the objective lens to spatially filter light from points other than the focal plane of the objective lens, which is within the liquid sample flow, before the light reaches the detector.

16. The method of claim 15 further comprising moving the illumination scanning mechanism to traverse the optical analysis region in an X vector perpendicular to a direction of the liquid sample flow and a Y vector parallel to the direction of the liquid sample flow.

17. The method of claim 16 including moving the illumination scanning mechanism in the Y vector at a velocity substantially equal to a velocity of the liquid sample flow.

18. The method of claim 15 further comprising controlling in real time the extent of the traverse in the X or Y direction or rate of traverse of the optical analysis region.

19. The method of claim 15 further comprising utilizing a lemniscate pattern to traverse the optical analysis region.

20. The method of claim 19 further comprising resetting the Y location of the optical scanner apparatus after each traverse in the X direction.

21. A method of conducting optical analysis comprising:
    (a) a sample delivery system comprising:
        (i) a delivery component for delivery of a liquid sample;
        (ii) a flow cell component defining a channel to which the liquid sample is delivered;

(b) illuminating the sample in an optical analysis region of the flow cell;
(c) controlling a controllable moveable scanning mechanism in a plurality of directions to substantially synchronize with the velocity of flow; and
(d) imaging at least a portion of the illuminated sample within the optical analysis region with an objective lens.

* * * * *